(12) United States Patent
Dick et al.

(10) Patent No.: US 9,056,054 B2
(45) Date of Patent: *Jun. 16, 2015

(54) ABUSE RESISTANT ORAL DOSAGE FORMS

(75) Inventors: Christopher C. Dick, New Hope, PA (US); David F. Erkoboni, Pennington, NJ (US); Charanjit R. Behl, Hauppauge, NY (US); Gary Bubb, Lebanon, NJ (US)

(73) Assignee: Elite Laboratories, Inc., Northvale, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/379,481

(22) PCT Filed: Jun. 25, 2010

(86) PCT No.: PCT/US2010/039947
§ 371 (c)(1),
(2), (4) Date: Mar. 15, 2012

(87) PCT Pub. No.: WO2010/151741
PCT Pub. Date: Dec. 29, 2010

(65) Prior Publication Data
US 2013/0084333 A1    Apr. 4, 2013

Related U.S. Application Data

(60) Provisional application No. 61/220,327, filed on Jun. 25, 2009.

(51) Int. Cl.
*A61K 9/28* (2006.01)
*A61K 9/20* (2006.01)
*A61K 31/485* (2006.01)

(52) U.S. Cl.
CPC .......... *A61K 9/28* (2013.01); *A61K 9/2095* (2013.01); *A61K 9/2846* (2013.01); *A61K 31/485* (2013.01); *A61K 9/2866* (2013.01); *A61K 9/2873* (2013.01); *A61K 9/2893* (2013.01)

(58) Field of Classification Search
CPC ... A61K 9/205; A61K 9/2846; A61K 31/485; A61K 9/2893; A61K 9/2866; A61K 9/2873; A61K 9/28
See application file for complete search history.

(56) References Cited

U.S. PATENT DOCUMENTS

| | | | |
|---|---|---|---|
| 6,419,959 B1 * | 7/2002 | Walter et al. | 424/490 |
| 8,182,836 B2 * | 5/2012 | Mehta | 424/457 |
| 2004/0056375 A1 | 3/2004 | Bubb | |
| 2004/0202717 A1 | 10/2004 | Mehta | |
| 2005/0191244 A1 * | 9/2005 | Bartholomaus et al. | 424/10.2 |
| 2006/0002860 A1 * | 1/2006 | Bartholomaus et al. | 424/10.1 |
| 2006/0039864 A1 * | 2/2006 | Bartholomaus et al. | 424/10.2 |
| 2008/0166405 A1 | 7/2008 | Mehta | |
| 2008/0233197 A1 * | 9/2008 | Matthews et al. | 424/490 |
| 2009/0022790 A1 * | 1/2009 | Flath et al. | 424/457 |
| 2009/0238868 A1 | 9/2009 | Mehta | |
| 2012/0189693 A1 * | 7/2012 | Dick et al. | 424/465 |

FOREIGN PATENT DOCUMENTS

| | | | | |
|---|---|---|---|---|
| WO | WO02087582 | * | 11/2002 | A61K 31/485 |
| WO | WO 2004/009319 A1 | | 1/2004 | |
| WO | WO 2008/114276 A1 | | 9/2008 | |
| WO | WO 2010/151741 A1 | | 12/2010 | |

OTHER PUBLICATIONS

Kibria et al. (Comparative study of aqueous dispersion of different types of polymers on release behavior of salbutamol sulphate from coated pellets, J. Pharm. Sci. & Resch., 2010, vol. 2, pp. 107-115).*

* cited by examiner

*Primary Examiner* — Bethany Barham
*Assistant Examiner* — Ping Cao
(74) *Attorney, Agent, or Firm* — Baker & Hostetler LLP

(57) ABSTRACT

Aspects of the present invention are directed to abuse resistant oral dosage forms comprising a compressed microtablet that is coated with a water-retardant polymer. Additional aspects of the present invention are directed to an oral dosage form comprising an opioid agonist and at least one compressed microtablet coated with a water retardant polymer. The compressed microtablet may comprise an opioid antagonist.

11 Claims, No Drawings

ABUSE RESISTANT ORAL DOSAGE FORMS

CROSS-REFERENCE TO RELATED APPLICATIONS

This application is the National Stage of International Application No. PCT/US2010/039947, filed Jun. 25, 2010, which claims the benefit of U.S. Provisional Application No. 61/220,327, filed Jun. 25, 2009, the disclosures of which are incorporated herein by reference in their entireties.

TECHNOLOGY FIELD

The present invention relates, inter alia, to oral, pain medication formulations and, in particular, to abuse-resistant formulations comprising a plurality of compressed microtablet/shell structures in which the compressed microtablet thereof includes an opioid antagonist.

BACKGROUND

Opioids (alternatively referred to as opioid agonists), are often used as analgesics for the regulation of perceived pain in a patient. Representative examples of opioids include oxycodone, morphine, hydrocodone, and codeine. Although opioids are effective at regulating perceived pain, there are some significant drawbacks to their use. Opioids, for example, are potentially physically and psychologically addictive to a patient if used repeatedly over an extended period of time. With respect to delayed release opioid dosage forms, there is an additional risk that individuals to whom they have been prescribed (and/or other individuals) will attempt to crush or grind the dosage forms to breach the structure(s) used to achieve delayed release, and then ingest the crushed or ground dosage forms to achieve the euphoria or "high" associated with relatively rapid uptake of the opioid.

One technique to reduce such abuse of opioid-containing dosage forms is to include an opioid antagonist. Opioid antagonists are drugs that serve to neutralize or block the euphoric or analgesic and overall physiological effect of an opioid agonist, for example, in individuals who have overdosed on an opioid agonist, or as a daily treatment drug in individuals who are addicted to an opioid agonist. It is thought that opioid antagonists act on and compete for the same receptor sites in the brain as opioid agonists, and thereby neutralize or block the resulting-analgesic or euphoric effects of the opioid agonist.

Various attempts have been made to reduce the risks of overdose on and addiction to opioid agonists. One approach has involved delivering both the opioid agonist and a suitable opioid antagonist in a single dosage form. For example, U.S. Publication No. 2004/0202717, the entirety of which is incorporated herein by reference, discloses opioid agonist dosage forms comprising inert beads that are coated, in turn, with an opioid antagonist and a polymer that controls release of the opioid agonist following oral ingestion but which releases the opioid antagonist upon breach when the dosage form is crushed or ground.

The use of traditional inert cores such as sugar non-pareils, microcrystalline cellulose beads, and wax beads as substrates to deliver pharmaceutically active agents has potential drawbacks. For example, water may diffuse drug loaded cores prepared using the sugar non-pareils or and microcrystalline cellulose beads, and cause an increase in osmotic pressure in the case of sugar non-pareils and swelling in the case of microcrystalline cellulose beads. In drug loaded cores bearing a coating to control release of the active agent, as water continues to diffuse into the core, the higher osmotic pressure or swelling could eventually rupture the coating and result in "dose dumping" of the active agent. Further, wax beads are temperature sensitive, which makes processing difficult, and it can be difficult to adhere a drug solution onto a wax bead. The pliable nature of wax beads generally makes them less effective for release of opioid antagonist if the dosage form is crushed or damaged; in fact, wax beads may actually aid in the opioid antagonist remaining sequestered.

Another drawback inherent in the use of inert cores to deliver active agents is that the presence of an inert material necessarily increases the size of the dosage form. Including inert beads at the core of a dosage form can also limit a formulator's ability to modify other components of the dosage form, such as the drug or the polymer coating. Accordingly, it would be highly desirable to provide an oral dosage form that is resistant to abuse but does not suffer from the drawbacks associated with the use of inert cores.

SUMMARY

In one aspect, the present invention is directed to oral dosage forms comprising a compressed microtablet that optionally bears a water-retardant polymer coating. The compressed microtablet preferably comprises at least about 0.05 weight percent of at least one opioid antagonist that is dispersed substantially throughout the compressed microtablet and/or releases no more than about 0.5 weight percent of the opioid antagonist within 36 hours when measured using the USP Apparatus (Basket) Method at 100 rpm at 37° C. in simulated gastric fluid for one hour followed by simulated intestinal fluid thereafter. Preferably, the opioid antagonist is naltrexone.

Other embodiments of the present invention are directed to methods of preventing the abuse of an oral dosage form of an opioid agonist comprising forming an oral dosage form by combining an opioid agonist and at least one compressed microtablet that is coated with a water-retardant polymer.

DETAILED DESCRIPTION OF ILLUSTRATIVE EMBODIMENTS

One aspect of the present invention provides oral dosage forms, i.e., dosage forms that are designed to be administered via the oral cavity of a patient to deliver one or more pharmaceutically active agents. Preferred dosage forms of the invention include at least one opioid (opioid agonist) and at least one opioid antagonist. Representative opioids include, for example, hydrocodone, morphine, hydromorphone, oxycodone, codeine, levorphanol, meperidine, methadone, oxymorphone, buprenorphine, fetanyl and derivatives thereof, dipipanone, heroin, tramadol, etorphine, dihyroetorphine, butorphanol, levorphanol, or mixtures thereof. Preferably, the opioid agonist comprises oxycodone. Representative opioid antagonists include naltrexone, naloxone, nalmephene, cyclazacine, levallorphan, and mixtures thereof. Preferably the opioid antagonist comprises naltrexone. A particularly preferred dosage form includes oxycodone and naltrexone. Suitable amounts of opioid antagonist may vary depending upon the opioid antagonist. For example, amounts of naltrexone suitable to block the euphoric effects of 40 mg of oxycodone typically are from about 0.04 mg to about 100 mg, preferably from about 2 mg to about 60 mg and most preferably 4 mg to 30 mg. Comparable ratios (e.g., from 0.001-1 to 2.5-1 naltrexone to oxycodone) can be used regardless of the dose of oxycodone.

It will be understood that a dosage form of the invention can itself include constituent dosage forms. Thus, for example, the present invention embraces dosage forms in which coated microtablets of opioid and opioid antagonist are contained within a gelatin capsule.

Preferred opioid antagonist dosage forms generally comprise a drug loaded compressed microtablet structure and a water-retardant polymer membrane. Compressed microtablets according to the invention can have virtually any shape and size, and typically have a major dimension that is in the range of about 0.5 to 3.0 mm, preferably about 0.5 to 2.0 mm, more preferably about 0.5 to 1.0 mm, even more preferably about 0.5 to 0.9 mm, and most preferably about 0.5 to 0.8 mm. However formed, compressed microtablets according to the invention comprise from about 0.01 to about 99.0 weight percent of at least one opioid antagonist, preferably from about 5 to about 60 weight percent, and most preferably from about 10 to about 45 weight percent.

In accordance with the present invention, the at least one opioid antagonist preferably is dispersed substantially throughout the compressed microtablet, i.e., dispersed such that there is no single volume within the compressed microtablet greater than about 0.003 cc that does not contain opioid antagonist. Such dispersion can be achieved by any of the techniques known in the art, such as, for example, by compressing a microtablet from a dry powder blend or wet granulation containing the opioid antagonist. The compressed microtablets of the invention thus are to be contrasted with prior dosage forms in which the active agent (even if present in an equivalent absolute amount) is disposed in a more localized (i.e. less dispersed) manner.

Such compressed microtablets preferably bear a membrane that comprises one or more water-retardant polymers. Preferably, the water-retardant polymer is physiologically acceptable, and substantially prevents the release of the opioid antagonist. In addition, the water retardant polymer may optionally be water insoluble. Representative classes of polymers include alkyl cellulose polymers, acrylic acid polymers, acrylic acid copolymers, methacrylic acid polymers, methacrylic acid copolymers, shellac, zein, or hydrogenated vegetable oil.

Suitable cellulose polymers include ethylcellulose, cellulose acetate, cellulose propionate (lower, medium, and higher molecular weight), cellulose acetate propionate, cellulose acetate butyrate, cellulose acetate phthalate, cellulose triacetate, cellulose ether, cellulose ester, cellulose, ester ether, cellulose, cellulose acrylate, cellulose diacylate, cellulose, triacylate, cellulose acetate, cellulose diacetate, cellulose triacetate, mono, di, and tricellulose alkanylates, mono, di, and tricellulose aroylates, mono, di, and tricellulose alkenylates, cellulose trivalerate, cellulose trilaurate, cellulose tripatmitate, cellulose trisuccinate, cellulose trioctanoate, cellulose disuccinate, cellulose dipalmitate, cellulose dioctanoate, cellulose dipentanoate, coesters of cellulose such as cellulose acetate butyrate, and cellulose acetate octanoate butyrate. Additional cellulose polymers include acetaldehyde dimethyl cellulose acetate, cellulose acetate ethylcarbamate, cellulose acetate methylcarbanate, and cellulose acetate dimethylaminocellulose acetate. In certain embodiments, suitable polymers include polylactic acid, polyglycolic acid, or a co-polymer of the polylactic and polyglycolic acid.

In certain embodiments, the water retardant polymer may be an acrylic polymer. Suitable acrylic polymers include acrylic acid and methacrylic acid copolymers, methylmethacrylate copolymers, ethoxyethyl methacrylate, cyanoethyl methacrylate, poly(acrylic acid), poly(methacrylic acid), methacrylic acid alkylamide copolymer, poly(methyl methacrylate), polymethacrylate, poly(methyl methacrylate) copolymer, polyacrylamide, aminoalkyl methacrylate copolymer, poly(methacrylic acid anhydride), and glycidyl methacrylate co-polymers. Preferably, the water-retardant polymer is physiologically acceptable, and substantially prevents the release of the opioid antagonist. In addition, the water retardant polymer may optionally be water insoluble. Preferred classes of water-retardant polymers include copolymers of methylmethacrylate and ethylacrylate and copolymers of acrylate and methacylates. Aqueous dispersions of such polymers are commercially available as Eudragit® RS 30D, Eudragit® RL 30D, Eudragit® NE 30D, Eudragit® NE 40D, and Eudragit® NM 30D from Evonik Rohm GmbH, Darmstadt, Germany. Particularly preferred are non-ionic poly(ethylacrylate-co-methylmethacrylate) polymers in which the molar proportions of the ethyl acrylate and methylmethacrylate monomer units, respectively, are in the ratio of about 2:1 and/or that have average molecular weights of about 800,000 Daltons (such as Eudragit® NE 30D, Eudragit® NE 40D, and Eudragit® NM 30D). Further examples of suitable water-retardant polymers include ethylcellulose from a solvent or as a dispersion, e.g., Aquacoat® ECD-30 from FMC Corp. or Surelease® form Colorcon, ammonio methacrylate copolymer Types A and B from granules (e.g. Eudragit® RS 100 and Eudragit® RL 100), powder (e.g., Eudragit® RS PO and Eudragit® RL PO) and dispersions (e.g. Eudragit® RS 30D and Eudragit® RL 30D), methacrylic acid copolymer, Type A and B from powder and dispersion (e.g., Eudragit® L100, Eudragit® S-100), and/or methacrylic acid copolymer, Type C (e.g., Eudragit® L100-55) and methacrylic acid copolymer dispersion (e.g., Eudragit® L30 D-55).

In certain embodiments, the oral dosage form may comprise between about 25 and about 800 weight percent increase after application of the membrane, preferably, between about 105 and about 500 weight percent increase, and more preferably between about 20 and about 400 weight percent increase. The weight increase results in a coated microtablet composition comprising between about 2 and about 89 weight percent of coating membrane, preferably, between about 9 and about 83 weight percent of coating membrane, and more preferably between about 16 weight percent and about 80 weight percent of coating membrane.

The membrane may be disposed directly upon the compressed microtablet or upon an intervening layer or structure. The membrane can be applied by any of the techniques known in the art. Typically, the compressed microtablet is coated with a solution of water-retardant polymer and the solvent is allowed to evaporate.

The membrane may optionally comprise a lubricant/anti-tacking agent such as, for example, calcium stearate, magnesium stearate, zinc stearate, stearic acid, glyceryl monostearate, hydrogenated vegetable oil, talc or a combination thereof. Preferably, the dried membrane contains between about 0.5 and about 200 weight percent increase lubricant/anti-tacking agent(s), more preferably between about 1 and about 100 weight percent increase, and most preferably between about 5 and about 50 weight percent increase. Preferably, the membrane contains an amount of magnesium stearate, or other lubricant, sufficient to provide non-release of the opioid antagonist for up to about 36 hours after administration of the dosage form to a human being. In a preferred embodiment, the membrane contains magnesium stearate admixed with the water-retardant polymer, preferably EUDRAGIT® NE-30D. The lubricant/anti-tacking agent may function to prevent agglomeration of opioid-antagonist-coated microtablets during processing and in some cases may also help to prevent release of the opioid antagonist from the oral dosage form. In other cases, it may lessen the ability of the membrane to prevent the release. Preferably, the membrane contains an amount of magnesium stearate, or other lubricant, sufficient to provide non-release of the opioid antagonist for up to about 36 hours after administration of the dosage form to a human being. Preferably, the dried membrane contains between about 1 and about 80 weight percent magnesium stearate, more preferably between about 5 and about 50 weight percent, and most preferably between about 10 and about 40 weight percent.

The opioid antagonist dosage forms of the invention preferably do not release the opioid antagonist for an extended period of time following ingestion by the patient. Ideally, the dosage form passes through the patient's system without producing an effective blood plasma concentration of the antagonist, or at least not for an extended period of time. For example, the opioid antagonist preferably is not detectable in blood at physiologically effective levels for up to about 1 day, preferably up to about 3 days, more preferably up to about 5 days. An alternative way to characterize the release properties of the dosage forms of the invention is by reference to in vitro test methods. Such dosage forms preferably release no more than about 0.5 weight percent of the opioid antagonist within 36 hours when measured using the USP Apparatus I (Basket) Method at 100 rpm at 37° C. in simulated gastric fluid for one hour followed by simulated intestinal fluid thereafter, more preferably no more than about 0.1 weight percent of the opioid antagonist within 36 hours under such conditions. It is preferable that such dosage forms release no more than the stated level within 96 hours under such conditions, with such release within 168 hours being even more preferable.

One class of compressed microtablets according to the invention is formed by compressing an antagonist-containing powder to form a microtablet. The compressed microtablets of the present invention have a size that makes them feasible for use in a capsule tablet or pill form. For example, the compressed microtablets may have a major dimension of between about 0.25 and about 1.0 mm. In a preferred embodiment, the compressed microtablets have a major dimension of between about 0.4 mm and about 0.9 mm. In a more preferred embodiment, the compressed microtablets have a major dimension of between about 0.5 mm and about 0.8 mm. As used herein the range of between about 0.25 and about 1.0 mm is inclusive. For example the recited range should be construed as including ranges "0.25 to 0.9', 0.25 to 0.8" 0.3 to 0.7", and the like. The compressed microtablets may have an aspect ratio (i.e., a ratio of major/longest dimension to minor/shortest dimension) of between about 1:0.5 and about 1:4, preferably between about 1:0.9 and 1:1.1. Preferably the compressed microtablet is substantially spherical. In certain embodiments, the compressed microtablets will comprise at least 0.01 weight percent opioid antagonist, or, for example, at least about 10 weight percent opioid antagonist, or, for example at least about 70 weight percent opioid antagonist.

Suitable compressed microtablets may be obtained by processes such as, for example, direct compression (blending and compression); high shear granulation, optionally milling, blending, and compression; fluid bed granulation, optionally milling, blending, and compression; roller compaction, optionally milling, blending, and compression; and slugging, optionally milling, blending, and compression. As an example, for direct compression the ingredients of the formulation can be blended in a suitable blender such as a V-type blender. The compressed microtablets can include, for example, binders, compression aids, glidants and lubricants. The blended materials are compressed on a tablet press that is modified for the use with tooling designed to compress suitably sized compressed microtablets. The compressed microtablets can then be coated to sequester opioid antagonist contained therein.

There are several benefits to using compressed microtablets as opposed to traditional inert cores. For example, the compressed microtablets may have a smoother outer surface than traditional inert cores coated with a drug, for example an opioid antagonist. A smoother surface leads to a more uniform membrane coating and a more consistent release in the case of controlled release microtablets and a more predictable and constant barrier to release in the case of non-release microtablets. Additionally, batches of compressed microtablets will have a relatively uniform size distribution while inert cores coated with opioid antagonist typically have a Gaussian distribution. An even size distribution will provide for a more consistent release profile, in the case of controlled release microtablets or barrier to release in the case of non-release microtablets, among the individual compressed microtablet dosing units contained in a batch as well as the units from a specific batch compared to other batches.

In practice, compressed microtablet cores will include not only the opioid antagonist but also at least one excipient. Suitable excipients include compression aids, binder agents, glidants, disintegrants, lubricants, or a combination thereof, among others. Suitable compression aids include microcrystalline cellulose, lactose, dicalcium phosphate, sucrose, starch, stearic acid, polyethylene glycol, waxes such as microcrystalline wax, carnuba wax and the like or a combination thereof, among others. Suitable binder agents include those included in the opioid antagonist layer and are described in detail herein. Suitable glidants include talc, silicon dioxide, or a combination thereof, among others. Suitable disintegrants include starch, croscarmellose sodium, crospovidone, sodium sarch glycolate or a combination thereof, among others. Suitable lubricants include calcium strearate, magnesium stearate, zinc stearate, strearic acid, talc, hydrogenated vegetable oil, or a combination thereof, among others. In addition, the compressed microtablets can bear suitable coating materials. In certain embodiments, the excipient(s) comprise between about 1 and about 99.99 weight percent of the oral dosage form. In a preferred embodiment, the excipient(s) may comprise between about 10 and about 75 weight percent of the oral dosage form. For example, the compressed microtablet may comprise between about 5 and about 99.99 weight percent compression aid, between about 0.5 and about 50.0 weight percent binding agent, between about 0.1 and about 20.0 weight percent glidant, between about 0 and about 20.0 weight percent of disintegrant, and between about 0.1 and about 20.0 weight percent lubricant.

Opioid antagonist compressed microtablets according to the invention may comprise an opioid antagonist coating or layer that comprises one or more opioid antagonists and a binding agent. The opioid antagonist layer may be coated onto the compressed microtablet, and the membrane may be coated onto the opioid antagonist layer. The binding agent may serve to enhance adherence of the opioid antagonist layer to the opioid antagonist compressed microtablet. Suitable binder agents include, for example, hypromellose, hydroxyethyl cellulose, hydroxypropyl cellulose, methyl cellulose, ethyl cellulose, polyvinyl pyrrolidone, polyvinyl alcohol, copovidone-copolymer of vinylpyrrolidone and vinyl acetate, a carbomer, amino methylacrylate copolymer, acrylic polymers and the like. In one preferred embodiment, hypromellose, and most preferably, hypromellose (6 cps) or Opadry® clear, which is an instantly water dispersible plasticized low molecular weight hypromellose product, is used in accordance with the invention. In another preferred embodiment polyvinyl alcohol is used in accordance with the invention. Preferably, the binder agent is dissolved in water (or any suitable solvent) to form a 5% to 30% (w/w) solution, preferably a 7% to 25% (w/w) solution and most preferably, an approximately 10% (w/w) solution. The binder solution may contain a plasticizing agent such as polyethylene glycol or propylene glycol among others, as examples, at a level of 1-30 weight percent based on the weight of dried solids in the solution. The solution of binder agent may be admixed with a solution or suspension of the opioid antagonist, and then applied onto the opioid antagonist compressed microtablet by conventional spray techniques. For example, the opioid antagonist layer may be applied to the opioid antagonist compressed microtablet by spraying the solution or suspension onto the compressed microtablet using a fluid bed processor.

The opioid antagonist layer may comprise between about 0.01 and about 99 weight percent opioid antagonist, preferably between about 10 and about 80 weight percent opioid antagonist, and more preferably, between about 20.0 and about 60.0 weight percent. In certain embodiments, the opioid antagonist layer may comprise between about 0.1 and about 50.0 weight percent of the oral dosage form, preferably between about 10.0 and about 30.0 weight percent.

Additionally, a sealing layer may be coated directly onto the opioid antagonist microtablet or opioid antagonist layer, or between the optional opioid antagonist layer and the membrane layer. The sealing layer may contain a water soluble polymer, which may be the same or different than the binder agent present in the opioid-antagonist layer. For example, the sealing layer may include a water soluble polymer such as hypromellose (preferably 3-6 cps), hydroxyethyl cellulose, hydroxypropyl cellulose, methyl cellulose, polyvinylpyrrolidone, polyvinyl alcohol and the like. Preferably, hypromellose (6 cps) and polyvinyl alcohol, and most preferably, polyvinyl alcohol is employed in the sealing layer. In addition, the sealing layer may optionally contain water an insoluble polymer, for example, ethylcellulose, a water soluble polymer dispersion, for example, an ethylcellulose dispersion (AQUACOAT® ECD as sold by FMC Corp. or SURELEASE® as sold by Colorcon), water soluble materials, for example, lactose, sucrose, polyethylene glycol, propylene glycol, a lubricant, such as, for example, calcium stearate, magnesium stearate, zinc stearate, stearic acid, talc, glyceryl monostearate, hydrogenated vegetable oil, or a combination thereof, and a plasticizer, for example, polyethylene glycol, propyklene glycol dibutyl sebecate, triethyl citrate, triacetin, diethyl citrate and the like, or combinations thereof. The optional sealing layer coated between the opioid antagonist and the membrane may comprise between about 0.5 and about 40 weight percent of the oral dosage form.

In another embodiment of the invention, the membrane is coated with an optional sealing layer. This optional sealing layer is similar to the previously described optional sealing layer between the opioid-antagonist pressed microtablet or layer and the membrane. The optional sealing layer may be comprised of the same elements as the sealing layer between the opioid antagonist pressed microtablet or layer and the membrane layer. The sealing layer may comprise a water soluble polymer, which may be the same or different from the binder agent present in the opioid-antagonist layer. For example, the sealing layer may include a water soluble polymer such as hypromellose (preferably 3 to 6 cps, more preferably 6 cps), hydroxyethyl cellulose, hydroxypropyl cellulose, methyl cellulose, polyvinylpyrrolidone, polyvinyl alcohol and the like. Preferably, hypromellose (6 cps) or polyvinyl alcohol, and most preferably, polyvinyl alcohol is employed in the sealing layer. In addition, the sealing layer may comprise a lubricant, such as, for example, calcium stearate, magnesium stearate, zinc stearate, stearic acid, talc, glyceryl monostearate hydrogenated vegetable oil, or a combination thereof. The total amount of the optional sealing layer contained in the oral dosage form is preferably between about 0.5 and about 40 weight percent.

The membrane may also be coated with an enteric layer comprising an enteric coating polymer. Suitable enteric polymer coatings include, for example, cellulose acetate phthalate from solvent or as aqueous dispersion, AQUACOAT® CAP (FMC Corp.) methacrylic acid copolymer dispersion, for example EUDRAGIT® L30D-55 (Evonik Industries), methacrylic acid copolymer dispersion Type A and B, for example, EUDRAGIT® L-100 and S-100 (Evonik Industries), hydroxymethylcellulose phthalate, polyvinyl acetate phthalate from solvent or as aqueous dispersion, SURETERIC® (Colorcon), or any combination thereof. The enteric layer may further comprise a plasticizer. Preferably, the enteric coating polymer is EUDRAGIT® S-100. Suitable plasticizers include, for example, triethyl citrate, polyethylene glycol, dibutyl phthalate, diethylphthalate and triacetin. The enteric layer, which is pH dependant and resistant to gastric fluids, preferably comprises between about 0.5 and about 40 weight percent of the oral dosage form. In other embodiments of the invention, the enteric layer may also be coated with a sealing layer the same or similar to the previously described sealing layers.

In another embodiment of the invention, the membrane (optionally coated with an enteric layer and/or a sealing layer) is coated with an opioid agonist layer comprising an opioid agonist. Any opioid agonist, or a pharmaceutically acceptable salt thereof, may be used in accordance with the invention. The opioid agonist layer may be formulated to release immediately or in a controlled fashion. In further embodiments, the opioid-agonist layer may also be coated with a sealing layer and/or an enteric layer similar to the sealing and enteric layers previously described.

Preferably, the opioid agonist is present in an amount to provide for effective blood plasma levels of the opioid agonist in a human being. That is, when the oral dosage form of the invention is orally administered to a human being, the opioid agonist will be released from the oral dosage form, and it can thus have its intended analgesic effect upon the human being. The amount of opioid agonist suitable to provide for effective blood levels may vary depending on the opioid agonist. For example, a suitable blood plasma level of oxycodone may be between about 5 ng/ml and about 300 ng/ml, preferably, between about 12 ng/ml and about 250 ng/ml.

When presented, for example, in a layer, the opioid-agonist may be applied with, for example, binder agents, diluents, carriers, fillers, lubricants and other pharmaceutically acceptable additives and excipients which may or may not effect the rate of release of the opioid agonist from the oral dosage form of this embodiment. Thus, any type of release profile known in the art, including but not limited to, immediate and sustained release formulations, may be used in accordance with the opioid-agonist layer of this embodiment.

The compressed microtablet comprising an opioid antagonist, the opioid antagonist layer, and/or the membrane of the invention may each further comprise diluents, carriers, fillers and other pharmaceutical additives which may or may not affect the rate of release of the opioid antagonist from the oral dosage form of the invention. For example, the membrane may comprise a lubricant and the opioid-antagonist layer may optionally contain a surfactant. The compressed microtablet, the opioid-antagonist layer, and/or the membrane may also further contain pharmaceutically acceptable excipients such as anti-adherents, and pharmaceutically acceptable pigments such as titanium dioxide, iron oxide and various color pigments including vegetable dyes, and the like.

In certain embodiments of the present invention, an oral dosage form may be in the form of a capsule and may comprise a combination of an opioid agonist contained in at least one compressed microtablet that is coated with a water-retardant polymer. The compressed microtablet may comprise at least about 99.0 weight percent of at least one opioid prior to the coating being applied and up to about 85 weight percent after the coating is applied and the dosage form may release no more than about 0.5 weight percent of said opioid antagonist within 36 hours when measured using the USP Apparatus I (Basket) Method at 100 rpm at 37° C. in simulated gastric fluid for one hour followed by simulated intestinal fluid thereafter. The compressed microtablet comprising the opioid antagonist may be in accordance with the oral dosage forms of the present invention. The opioid agonist may be made in accordance with techniques disclosed herein or known to those skilled in the art such as, for example, inert beads coated with the opioid agonist. The inert beads coated with the opioid agonist may further comprise a coating with an extended release polymer and may optionally comprise a sealing layer, an enteric layer, and additives such as binder agents, diluents, carriers, fillers, lubricants, and other pharmaceutically acceptable additives and excipients. In other embodiments, the opioid agonist may comprise a compressed microtablet comprising an opioid agonist. For example, the compressed microtablet may comprise an opioid agonist compressed microtablets having a diameter of between about 0.25 and about 3 mm, preferably between about 0.25 and about 1 mm, more preferably between about 0.5 and about 0.8 mm, or an extruded and spheronized matrix.

Compressed microtablets of the present invention may be formed at a rate of production that is suitable for commercial exploitation. For example, microtablets with a diameter of about 1 mm or less preferably are formed at a rate that is greater than about 10,000 microtablets per minute, more preferably greater than about 300,000 microtablets per minute, even more preferably greater than about 600,000 microtablets per minute.

The present invention is further defined in the following Examples, in which all parts and percentages are by weight, unless otherwise stated. It should be understood that these examples, while indicating preferred embodiments of the invention, are given by way of illustration only. From the above discussion and these examples, one skilled in the art can ascertain the essential characteristics of this invention, and without departing from the spirit and scope thereof, can make various changes and modifications of the invention to adapt it to various usages and conditions.

EXAMPLES

Example 1

Preparation of Uncoated Naltrexone Pressed Microtablets

Pressed microtablets containing a homogeneous dispersion of naltrexone are prepared by direct compression as described below. The ingredients include naltrexone, 444.44 g, lactose, hydrous (Foremost) 545.56 and magnesium stearate (Mallinckrodt), 10 g. All excipient materials are screened through a 20 mesh prior to use. The naltrexone is screened through a 40 mesh.

The naltrexone and lactose are charged into a 16 qt V-type blender and blended for a period of 15 minutes. The magnesium stearate is added to the mixture and blended for an additional 5 minutes. The dry blended materials are then charged into the hopper of a Picolla tablet press fitted with tooling designed to produce two or more compressed microtablets per punch, with each microtablet being almost spheroidal with a length of 0.85 mm and a mean diameter of 0.85 mm. This is achieved by orienting the microtablets substantially adjacent one another within the plane of the die such that the punch cavity is approximately 0.42 mm deep and 1.73 mm wide with a bisect of 0.03 mm with tooling designed to produce 2 compressed microtablets. The microtablets are compressed to a breaking force (hardness) of approximately 5 to 10 Newtons.

Example 2

Preparation of Uncoated Naltrexone Pressed Microtablets

Pressed microtablets containing a homogeneous dispersion of naltrexone are prepared by wet granulation as described below. The ingredients include naltrexone, 90.0 g, lactose, hydrous (Sheffield) 450.0, polyvinyl alcohol (Colorcon) 60.0 g, purified water 35.0 g, fumed silica (Cabot) 6.0 g and magnesium stearate (Mallinckrodt), 6.0 g. All excipient materials are screened through a 20 mesh prior to use. The naltrexone is screened through a 40 mesh.

The naltrexone, lactose and polyvinyl alcohol are charged into a 5 qt planetary mixer and mixed dry for 5 minutes. Purified water is added over a period of 5 minutes with mixing. After the purified water is added, the mixing is continued for a period of 20 minutes. The granulation is discharged onto a paper lined tray and placed in an oven at 50 degrees Celsius for a period of 16 hours. After 16 hours the dried granules are removed from the oven and passed through a 30 mesh US standard screen. The screened granules, silica and magnesium stearate are charged into a blender and blended for a period of 5 minutes. The blended materials are then charged into the hopper of a Piccola tablet press fitted with tooling designed to produce compressed microtablets having a diameter of 0.87 mm. The tools comprising a lower punch body, upper punch body, lower pin holder, upper pin holder, eighty-seven upper pins and eighty-seven lower pins and a die and compressed at a pressure of 10 to 500 MPa.

Example 3

Preparation of Coated Naltrexone Pressed Microtablets

Coated pressed microtablets are prepared as described below. The ingredients include the pressed microtablets from Examples 1 or 2, 900 g, dimethicone 30% dispersion (MFG) 37.8 g, magnesium stearate (Mallinckrodt) 558.2 g, ethyl acrylate and methyl methacrylate copolymer dispersion 30% (Evonik) 6201.3 g, purified water 9402.7 g.

Purified water is charged into a suitable stainless steel container fitted with an overhead mixer. The simethicone dispersion is added to the water with stirring followed by the magnesium stearate with continued stirring to form a magnesium stearate dispersion. The container containing the magnesium stearate dispersion is placed into a larger stainless steel container and the larger container is used as a jacket. Cold water is charged into the outer container to maintain the magnesium stearate dispersion at 20-26° C. during the homogenization step. The magnesium stearate dispersion is then homogenized for a period of 1 hour using an overhead homogenizer with a 4 inch head (Silverson model DX60).

The ethyl acrylate and methyl methacrylate copolymer dispersion is passed through a 60 mesh screen to remove any particulates. It is then added slowly with stirring to the magnesium stearate dispersion. The total dispersion is mixed for another 60 minutes prior to use.

The naltrexone pressed microtablets are charged into the Wurster bowl of a Glatt GPCG-3 fluid bed. The microtablets are fluidized using a sufficient air volume at a temperature to maintain the product at 24° C. The ethyl acrylate and methyl methacrylate copolymer/magnesium stearate dispersion is sprayed at a rate of approx. 3.5 g/min/kg for the first 30 minutes and a rate of 6-20 g/min/kg thereafter. The dispersion is sprayed until a percent weight gain of 260% is achieved. The product is dried for 3 minutes without spray while maintain a product temperature of approximately 24° C. and then discharged.

What is claimed:

1. A compressed microtablet that is coated with a membrane, the membrane comprising
    about 16 weight percent to about 80 weight percent, by weight of the membrane, of a water-retardant polymer that is a copolymer of methylmethacrylate and ethylacrylate; and
    about 5 weight percent to about 50 weight percent, by weight of the membrane, of an additive that is calcium stearate, magnesium stearate, zinc stearate, stearic acid, glyceryl monostearate, hydrogenated vegetable oil, talc, or a combination thereof;
    wherein said microtablet has a major dimension that is about 0.5 to about 3.0 mm and comprises about 10 to about 30 weight percent, by weight of the microtablet, of at least one opioid antagonist that is dispersed substantially throughout said microtablet,
    wherein the water retardant polymer is a non-ionic poly (ethylacrylate-co-methacrylate) polymer in which the molar ratio of the ethyl acrylate to methyl methacrylate is about 2:1;
    wherein the weight gain of the microtablet after the application of the membrane is from about 105 to about 500 weight percent increase;
    and said compressed microtablet releases no more than about 0.5 weight percent of said opioid antagonist within 36 hours when measured using the USP Apparatus I (Basket) Method at 100 rpm at 37° C. in simulated gastric fluid for one hour followed by simulated intestinal fluid thereafter.

2. The compressed microtablet of claim 1 wherein the opioid antagonist comprises naltrexone.

3. A capsule comprising the compressed microtablet of claim 1.

4. A method comprising providing at least one compressed microtablet according to claim 1, and combining an opioid agonist with the at least one compressed microtablet to form a dosage form, wherein said dosage form releases no more than about 0.5 weight percent of said opioid antagonist within 36 hours when measured using the USP Apparatus I (Basket) Method at 100 rpm at 37° C. in simulated gastric fluid for one hour followed by simulated intestinal fluid thereafter.

5. The compressed microtablet of claim 1, wherein the additive is magnesium stearate.

6. The compressed microtablet of claim 1, wherein the additive is talc.

7. The compressed microtablet of claim 1, wherein the water retardant polymer has average molecular weight at about 800,000 Daltons.

8. The compressed microtablet of claim 7, wherein the water retardant polymer is 30% aqueous dispersion of poly (ethyl acrylate-co-methyl methacrylate) (EUDRAGIT® NE 30 D).

9. The compressed microtablet of claim 1, wherein the membrane comprises about 10 to about 40 weight percent, by weight of the membrane, of the additive.

10. The compressed microtablet of claim 1, further comprising a sealing layer coating.

11. The compressed microtablet of claim 7 wherein the weight gain of the microtablet after the application of the membrane is about 260 weight percent increase.

* * * * *